(12) United States Patent
Nallakrishnan

(10) Patent No.: US 8,578,613 B2
(45) Date of Patent: Nov. 12, 2013

(54) SAFETY KNIFE WITH CURVED GUARD

(76) Inventor: Ravi Nallakrishnan, Westmont, IL (US)

( * ) Notice: Subject to any disclaimer, the term of this patent is extended or adjusted under 35 U.S.C. 154(b) by 170 days.

(21) Appl. No.: 12/904,985

(22) Filed: Oct. 14, 2010

(65) Prior Publication Data

US 2011/0092994 A1  Apr. 21, 2011

Related U.S. Application Data

(60) Provisional application No. 61/252,948, filed on Oct. 19, 2009.

(51) Int. Cl.
*B26B 3/06* (2006.01)

(52) U.S. Cl.
USPC ................................. 30/151; 30/162; 30/135

(58) Field of Classification Search
USPC ........ 30/151, 162, 335, 329, 2, 339; 606/162, 606/163, 335, 167, 166
See application file for complete search history.

(56) References Cited

U.S. PATENT DOCUMENTS

| | | | | |
|---|---|---|---|---|
| 4,569,133 A * | 2/1986 | Schmidt | ........................ | 606/172 |
| 4,896,983 A * | 1/1990 | Im et al. | ........................ | 401/107 |
| 5,234,436 A * | 8/1993 | Eaton et al. | ................... | 606/107 |
| 5,312,413 A * | 5/1994 | Eaton et al. | ................... | 606/107 |
| 5,749,886 A * | 5/1998 | Abidin et al. | ................. | 606/182 |
| 7,022,128 B2 * | 4/2006 | Morawski et al. | ............ | 606/167 |
| 7,445,624 B2 * | 11/2008 | Freier et al. | ................... | 606/167 |
| 8,136,251 B2 * | 3/2012 | Endo | ............................... | 30/162 |
| 8,157,797 B2 * | 4/2012 | Boukhny et al. | ................ | 606/45 |
| 8,256,331 B2 * | 9/2012 | Auchter et al. | ................... | 83/13 |
| 2008/0058844 A1 * | 3/2008 | Morawski et al. | ............ | 606/167 |
| 2010/0125290 A1 * | 5/2010 | Auchter et al. | ............... | 606/167 |

* cited by examiner

*Primary Examiner* — Omar Flores Sanchez
(74) *Attorney, Agent, or Firm* — Jerry A. Schulman

(57) ABSTRACT

A safety knife for ophthalmic surgical procedures has handle to which a blade holder is attached at one end, holding a pre-installed surgical blade. A blade guard is extended and retracted responsive to the movement of an actuator button on the handle. The blade assumes a curved shape as it is extended, to shape itself about and protect the blade. When the guard is retracted it straightens to allow it to slide into the handle, exposing the blade for use.

7 Claims, 4 Drawing Sheets

SAFETY KNIFE WITH CURVED GUARD

This application claims priority from U.S. patent application Ser. No. 61/252,948, filed Oct. 19, 2009 and entitled "Safety Knife With Curved Guard" which is incorporated herein in its entirety by reference for all purposes as if fully set forth herein.

The present invention relates to knives used for surgery and, in particular, a safety surgical knife having a retractable blade guard that can be extended to protect the blade and retracted to expose the blade for use. The retracting mechanism is placed and designed to allow a user to manipulate the guard without changing the user's hand position.

BACKGROUND OF THE INVENTION

Knives and scalpels used in ophthalmic surgery have small and extremely sharp blades. During eye surgery it is desirable to make the incisions as small as possible to allow for faster healing and to obviate the need for stitching the incision closed after surgery has been completed.

Surgical instruments are typically arranged by a surgical assistant and passed to the surgeon as needed. When the surgeon is finished using a particular instrument, it is customary for the surgeon to pass the instrument back to the assistant who then retains it for further use or, if use is completed, disposes of the instrument.

Operating in as confined a surgical field as the eye requires dexterity, concentration and, often, the use of microscopes or other magnifying devices to allow the surgeon to more clearly visualize the eye tissue. A constant concern during surgical procedures is the accidental cutting of either the surgeon or the assistant by an exposed cutting blade. Accidental cutting may cause serious injury and will also require that the person cut be regloved before surgery can continue.

It is known to provide scalpels and knives with blade covers or blade guards to protect the blade itself prior to surgery and to protect the blade users during surgery. Examples of such blade guards are found in the prior art.

U.S. Pat. No. 7,022,128 (Morawsky) teaches and describes a surgical knife safety handle having a blade guard that can be extended from and retracted into the handle.

U.S. Pat. D496,730 (Morawsky et al) teaches and describes an ornamental design for surgical knife safety handle corresponding to the knife described and claimed in the '128 patent.

U.S. Pat. No. 6,626,925 (Newman et al) teaches and describes a shielded surgical scalpel having an extendable and retractable blade guard.

A common drawback to the designs shown in the aforementioned references is the necessity for the surgeon to maintain either an uncomfortable hand position during retraction and extension of the guard, or the need for the surgeon to grip the knife in a first position to operate the blade guard, then change grips to use the knife to make incisions. Repositioning the surgeon's hand after retracting the guard often means that the surgeon's attention and concentration is drawn away from the operating field and to the knife itself.

It is good surgical procedure to have the guard in place when the knife is passed back and forth between the assistant and the surgeon. Prior knife designs tend to require the surgeon's hand to be repositioned when the surgeon's use of the knife is completed to extend the guard before passing it back to the surgical assistant.

Commonly, the assistant already has the next instrument to be used in one hand ready to pass to the surgeon, while receiving the used instrument in the other hand. It would be awkward and dangerous for the surgical assistant to take a knife with the guard retracted and use a single hand to extend the guard before disposing of the knife.

Prior art safety handle designs thus make the extension and retraction of the guard awkward and uncomfortable without repositioning the user's hand.

The present invention provides a safety knife with a retractable and extendable guard and a mechanism designed to allow the movement of the guard without repositioning the user's hand from a comfortable cutting position.

The present invention also provides a guard having a simple, uncomplicated design, the guard being moveable to a fully retracted position where no part of the guard extends past the handle end, leaving the surgeon with a clear and complete view of the blade during surgery.

The present design also provides a guard which allows the blade to be viewed directly even when the guard is in its fully extended and protective position.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

These and further aspects of the present invention will best be appreciated upon considering the accompanying drawing wherein.

DETAILED DESCRIPTION OF THE INVENTION

Figure 1:
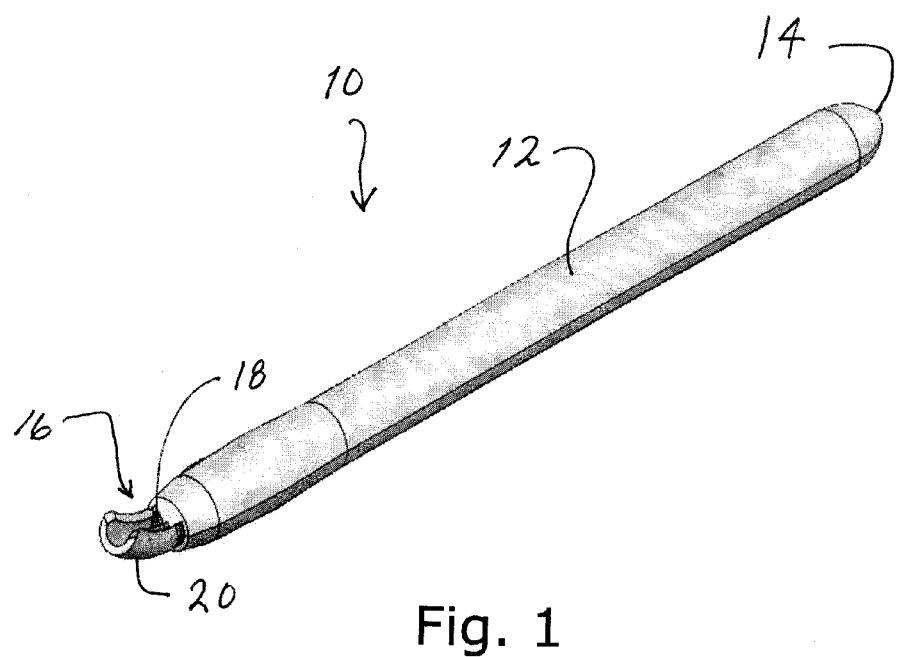
FIG. 1 is a perspective view of a surgical knife embodying certain principles of the present invention with the blade guard extended.

Referring now to FIG. 1, the numeral 10 identifies a surgical safety knife having a handle 12 with a proximal end 14 and a distal end 16. A blade assembly 18 extends from distal end 16 and a blade guard 20 also extends from distal end 16 to partially surround blade assembly 18.

Figure 2:
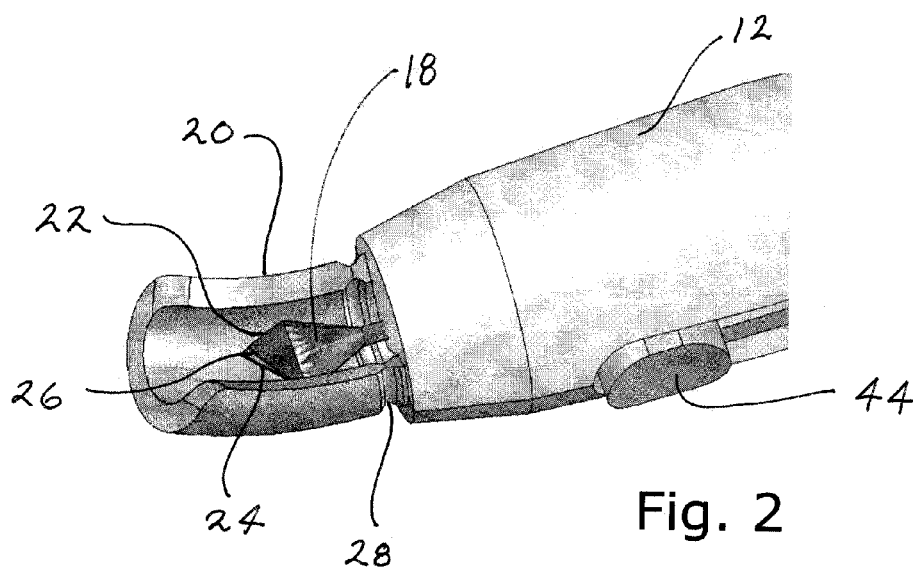
FIG. 2 is an enlarged detail view of a portion of the knife of FIG. 1.

Referring now to FIG. 2, blade assembly 18 is shown in further detail having cutting edges 22, 24 meeting at a blade apex 26. As seen in FIG. 2 and as described in more detail hereinbelow, guard 20 is curved when extended and has an accordion-type living hinge 28 formed thereon.

Figure 3:
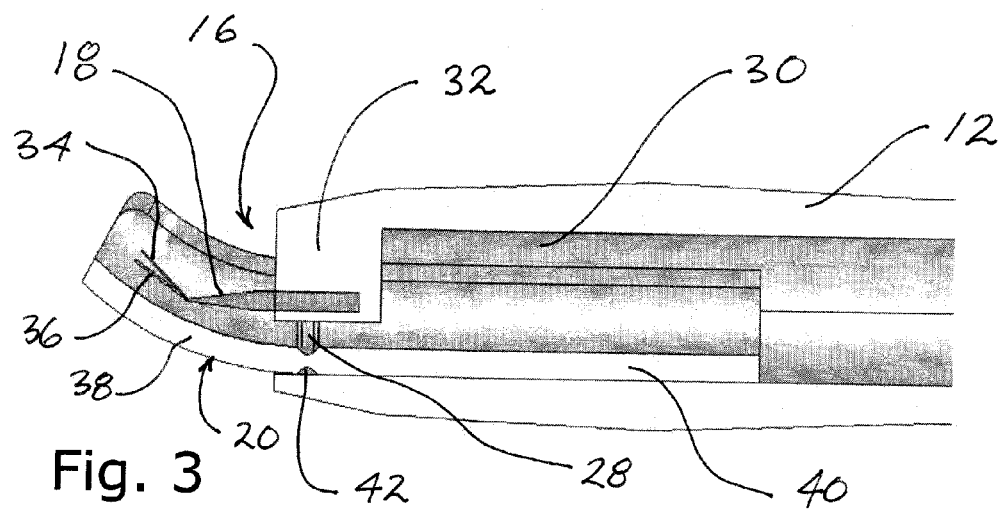
FIG. 3 is a partial sectional view of a portion of the knife of FIG. 1.

Referring now to FIG. 3, knife 10 is shown in a partial lateral sectional view. In this view, it can be seen that handle 12 is hollow, having a cylindrical channel 30 terminating at a guide block 32 formed at distal end 16. In the embodiment shown, blade assembly 18 is embedded in or mounted to guide block 32. Blade assembly 18 will typically include either a 45 degree blade 34 or a 30 degree blade 36; both are shown to demonstrate the positioning of each with respect to guard 20.

As also shown in FIG. 3, guard 20 has a first curved portion 38 formed contiguously with a straight portion 40 with hinge 28 formed at the juncture of curved section 38 and straight portion 40. A guard notch 42 is preferably formed about the outer periphery of guard 20 substantially parallel to and opposite from hinge 28.

Figure 4:
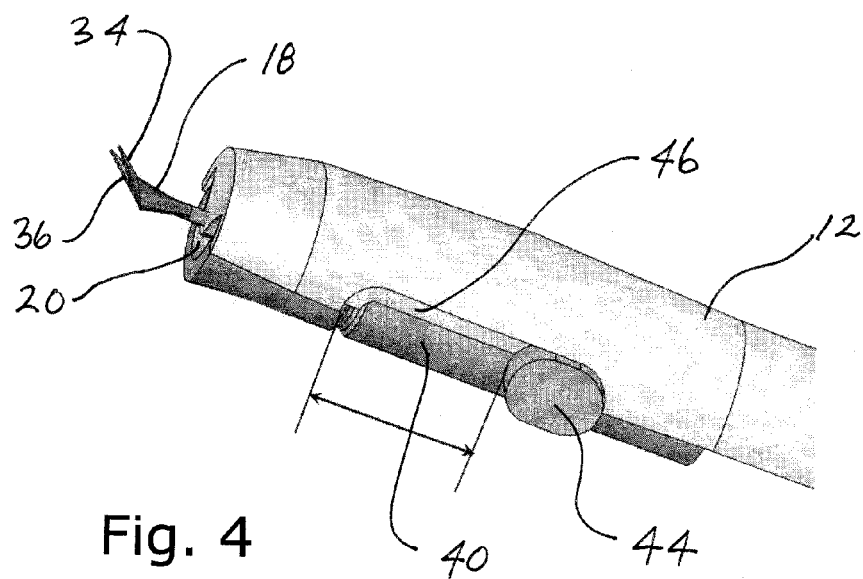
FIG. 4 is a perspective view of the knife of FIG. 1 with the blade guard fully retracted.

Referring now to FIG. 4, a detail of knife 10 is shown with guard 20 fully retracted to expose blade assembly 18. Again, as shown, blade assembly 18 illustrates the placement of either a 45 degree blade 34 or a 30 degree blade 36.

As seen in FIG. 4, a button 44 is formed integrally with straight portion 40 of guard 20. As further seen, handle 12 has a slot 46 formed therethrough from which button 44 protrudes and within which button 44 can be longitudinally moved. As seen in FIG. 4, button 44 can be moved proximally to fully retract guard 20 into handle 12. Conversely, as seen in FIG. 2, button 44 can be moved distally to extend guard 20 from handle 12.

As further seen in FIG. 4, slot 46 is preferably formed with a slot seat 58 within which button 44 is partially held and which guides button 44 in a straight fore and aft direction when button 44 is moved.

Figure 5:
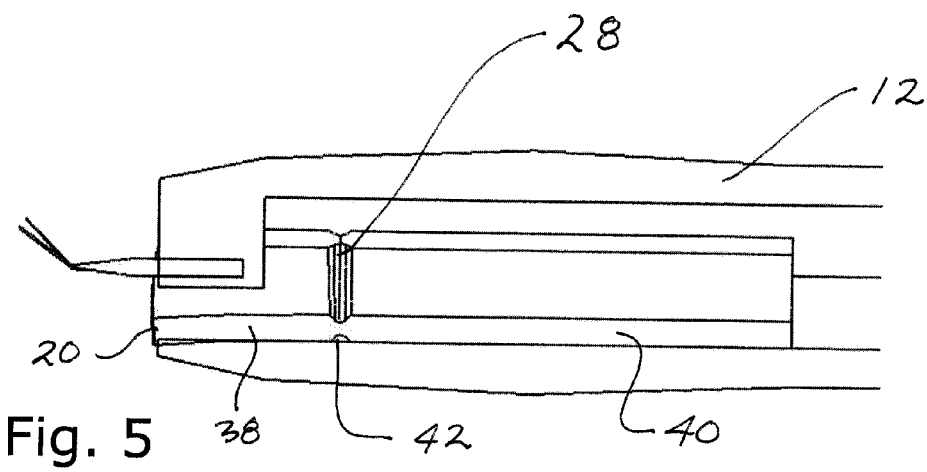
FIG. 5 is a lateral plan view of the detail of FIG. 4 illustrating the use of blades at different angles.

Referring now to FIG. 5, handle 12 is shown with guard 20 fully retracted and illustrates the relative position of curved portion 38 and straight portion 40. As seen, hinge 20 and notch 42 provide sufficient play for curved portion 38 to be moved to a substantially straight position in order to allow curved portion 38 to be fully retracted into handle 12. Preferably, guard 20 is constructed such that curved guard portion 38 takes its curved shape when unstressed.

Figure 6:
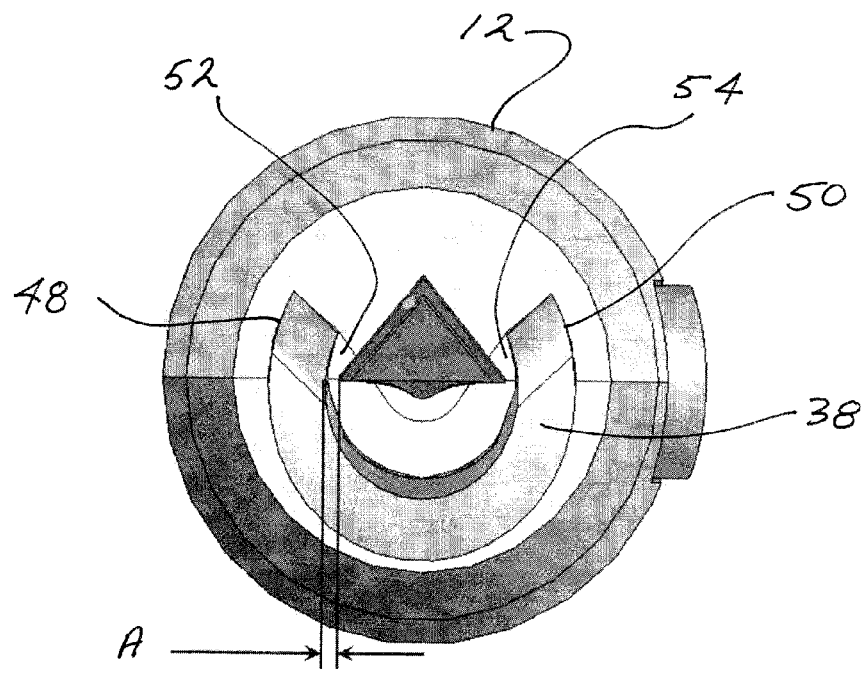
FIG. 6 is a view along 6-6 of FIG. 1.

Referring now to FIG. 6, curved guard portion 38 is shown fully withdrawn into handle 12. Preferably, guard 38 is formed with a generally U-shaped cross section terminating at upper edges 48, 50. As seen in FIG. 6, guide 32 has a pair of guide channels 52, 54, sized and shaped to receive curved guard portion 38 and to keep guard portion 38 moving in a straight line when extended from or retracted into handle 12.

As seen in FIG. 6, curved guard portion 38 is sized and shaped to provide a clearance distance A between curved portion 38 and blade assembly 18, preferably at least 0.75 mm.

Figure 7:
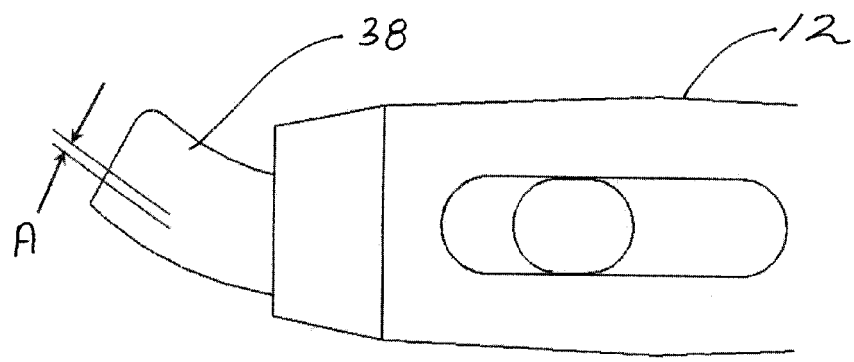
FIG. 7 is a partial lateral plan view of the detail of FIG. 2.

Referring now to FIG. 7, clearance distance A is also shown to obtain when curved portion 38 is extended from handle 12.

Figure 8:
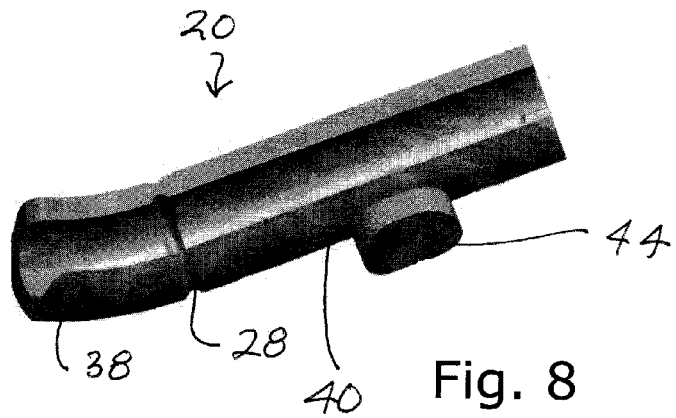
FIG. 8 is a perspective view of the curved guard.

Referring now to FIG. 8, guard 20 is shown removed from handle 12. Preferably, guard 20 and button 44 are made as a single piece with button 44 extending from straight portion 40. FIG. 8 shows the curved shape guard portion 38 assumes when unstressed, beginning at hinge 28.

Figure 9:
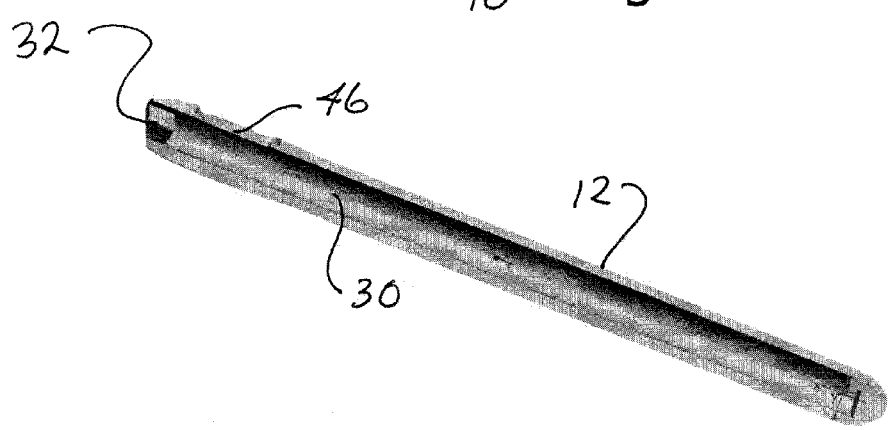
FIG. 9 is a perspective view of a portion of the handle.

Referring now to FIG. 9, handle 12 is shown in a sectional perspective view, with channel 30 visible, extending the length of handle 12. Also visible is guide block 32 and a portion of slot 46.

Use of the present invention may now be described. Knife 10 is provided with guard 20 fully extended. Blade assembly 18 is substantially surrounded by curved portion 38 of guard 20 with cutting edges 22, 24 and apex 26 protected while still allowing the surgeon to visually view and inspect blade assembly 18. In this position, knife 10 is preferably transferred from the surgical assistant to the surgeon. The surgeon then grips handle 12 of knife 10. Preferably, slot 46 and button 44 are positioned such that when the surgeon grips handle 12, he is holding it in the position that he would normally hold it in order to use blade assembly 18 during surgery.

The surgeon next uses his thumb to slide button 44 toward the proximal end of handle 12, thus retracting curved portion 38 of guard 20 into handle 12. During the retraction process, curved portion 38 is held and guided by guide slots 52, 54 formed in guide block 32.

After the surgeon has completed this use of knife 10, the surgeon then uses his thumb to advance button 44 toward the proximal end 16 of handle 12 thereby extending curved portion 38 of guard portion 20 to surround and protect blade assembly 18.

When guard 20 is retracted, curved portion 38 straightens at hinge 28 allowing curved portion 38 to be drawn longitudinally into handle 12. Conversely, when button 44 is used to advance guard 20 from handle 12, curved portion 38 progressively regains its curved orientation until fully extended.

In this manner, both surgeon and assistant can conveniently and effectively extend and retract guard 20 using one hand without requiring repositioning of the hand.

What is claimed is:

1. A safety knife, said knife comprising:
    a hollow, substantially cylindrical handle having a distal end, a proximal end and a central, longitudinally-extending handle axis;
    said handle defining a chamber therein,
    said chamber open at said distal end;
    a knife blade holder secured to said handle at said distal end;
    a knife blade secured to said holder with at least a portion of said knife blade having cutting edges, said cutting edges exposed and extending outward past said distal end;
    a guard positioning mechanism disposed slidably within said chamber; and
    a blade guard,
    said blade guard being movable from a fully retracted position within said chamber to an extended position from said distal end and past said knife blade responsive to the movement of said guard positioning mechanism,
    said blade guard assuming a curved shape to surround at least a portion of said knife blade exposed portion, when moved to said extended position, without touching said blade exposed portion,
    said blade guard exposing said cutting edges for use when said blade guard is moved to said fully retracted position.

2. The apparatus as recited in claim 1 wherein said handle has a slot formed therein, said slot communicating with said chamber; and
    said guard mechanism further comprises a control button,
    said control button extending from said chamber through said slot;
    said guard mechanism and, thereby, said guard, extending and retracting responsive to the movement of said button along said slot.

3. The apparatus as recited in claim 1 wherein said blade guard further comprises:
    a straight portion; and
    a curved portion,
    said curved portion being deformable to a substantially straight configuration.

4. The apparatus as recited in claim 3 wherein said knife blade holder further comprises a holder body,
  said holder body configured to close off a portion of said distal end;
  said holder body and said handle defining a holder body guide slot,
  said guide slot shaped and dimensioned to allow said curved portion of said guard to be extended from and retracted into said chamber.

5. The apparatus as recited in claim 4 wherein said holder body is formed as a single piece with said handle.

6. The apparatus as recited in claim 3 wherein said blade guard further comprises:
  at least one groove formed where said curved and straight guard portions meet,
  said groove forming a hinge whereby said curved portion can assume a curved portion with respect to said straight portion.

7. The apparatus as recited in claim 6 wherein a plurality of said grooves are formed in a pleated configuration.

\* \* \* \* \*